(12) United States Patent
Xu et al.

(10) Patent No.: US 9,927,620 B2
(45) Date of Patent: Mar. 27, 2018

(54) SYSTEM FOR FLAT-TOP INTENSITY LASER SHEET BEAM GENERATION

(71) Applicant: Intel Corporation, Santa Clara, CA (US)

(72) Inventors: Shengbo Xu, Newark, CA (US); Tolga Acikalin, San Jose, CA (US)

(73) Assignee: INTEL Corporation, Santa Clara, CA (US)

( * ) Notice: Subject to any disclaimer, the term of this patent is extended or adjusted under 35 U.S.C. 154(b) by 55 days.

(21) Appl. No.: 14/859,489

(22) Filed: Sep. 21, 2015

(65) Prior Publication Data

US 2017/0082861 A1    Mar. 23, 2017

(51) Int. Cl.

| G02B 3/06 | (2006.01) |
|---|---|
| G02B 27/09 | (2006.01) |
| G02B 19/00 | (2006.01) |
| H01S 5/00 | (2006.01) |
| G02B 3/04 | (2006.01) |
| G01N 15/02 | (2006.01) |
| G01N 15/00 | (2006.01) |

(52) U.S. Cl.
CPC ..... *G02B 27/0927* (2013.01); *G01N 15/0211* (2013.01); *G02B 3/04* (2013.01); *G02B 3/06* (2013.01); *G02B 19/0014* (2013.01); *G02B 19/0052* (2013.01); *H01S 5/005* (2013.01); *G01N 2015/0046* (2013.01)

(58) Field of Classification Search
CPC ................................................. G02B 27/0966
USPC ......................................................... 359/710
See application file for complete search history.

(56) References Cited

U.S. PATENT DOCUMENTS

| 5,373,395 | A | 12/1994 | Adachi |
|---|---|---|---|
| 6,246,524 | B1 | 6/2001 | Tanaka |
| 7,400,457 | B1 | 7/2008 | Cayer |
| 9,285,593 | B1 * | 3/2016 | Laskin ............... G02B 27/0927 |
| 2008/0144194 | A1 | 6/2008 | Tanaami et al. |
| 2015/0160468 | A1 * | 6/2015 | Ma ..................... G02B 27/0025 |
|  |  |  | 359/641 |

FOREIGN PATENT DOCUMENTS

CN        201805141 U    4/2011

OTHER PUBLICATIONS

Laskin, Alexander, "Solutions for Beam Shaping, Control of laser intensity profile and spot shape with refractive beam shaping," LTJ, Jan. 2013, No. 1. pp. 37-40.

(Continued)

*Primary Examiner* — James Jones
(74) *Attorney, Agent, or Firm* — Finch & Maloney PLLC

(57) ABSTRACT

Systems and techniques are disclosed for flat-top intensity laser sheet beam generation. The system includes a source of light directed at a first optical component arranged to receive the light and generate spherical aberration (e.g., third order positive aberration) in the light rays. The spherical aberration results in positive aberrations in the light in a first plane and also results in the light being substantially collimated in a second plane perpendicular to the first plane. In some cases, the source of light is provided from a laser diode and the first optical component is one of an aspherical lens and a spherical lens. The system also includes a second optical component for focusing the light in the second plane. In some cases, the second optical component is a cylindrical lens.

17 Claims, 3 Drawing Sheets

(56) References Cited

OTHER PUBLICATIONS

U.S. Appl. No. 15/132,452, filed Apr. 19, 2016. 55 pages.
International Search Report and Written Opinion received for Patent Application No. PCT/US2016/042447, dated Oct. 19, 2016. 15 pages.

* cited by examiner

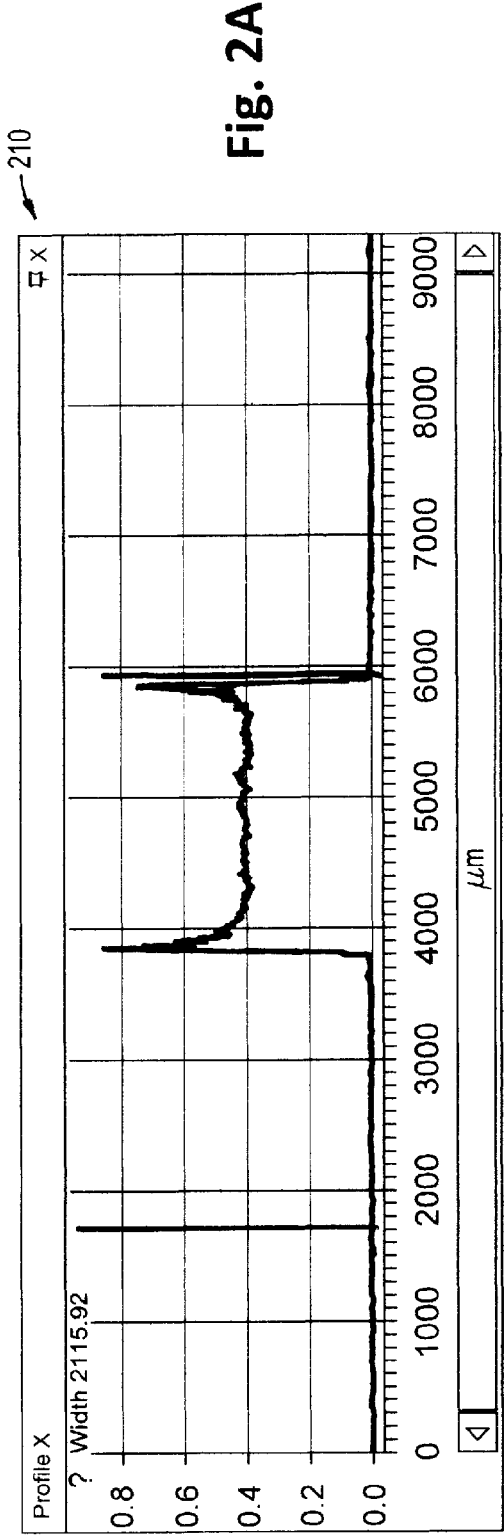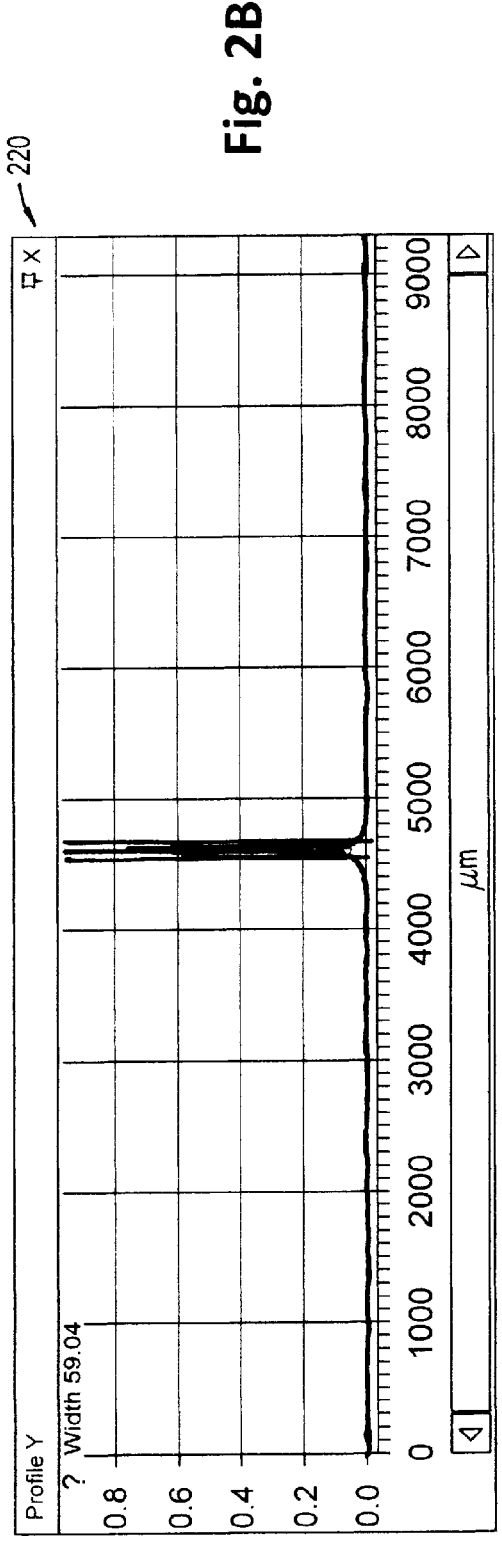

SYSTEM FOR FLAT-TOP INTENSITY LASER SHEET BEAM GENERATION

BACKGROUND

A laser is a device that emits light through a process of optical amplification based on the stimulated emission of electromagnetic radiation. A laser differs from other sources of light in that it emits light coherently. Spatial coherence allows a laser to be focused to a tight spot, enabling applications such as laser cutting and lithography. Although there are different spatial modes for laser light, the most common is the TEM00 mode in which laser light is generated with a Gaussian intensity profile. A Gaussian intensity profile or Gaussian beam has transverse electric field and intensity (irradiance) distributions that are well approximated by Gaussian functions.

BRIEF DESCRIPTION OF THE DRAWINGS

FIGS. 2A-B illustrate example plots showing experimental results validating the flat-top intensity laser sheet generation of the system of FIGS. 1A-B, in accordance with an embodiment of the present disclosure.

DETAILED DESCRIPTION

Figure 1A:
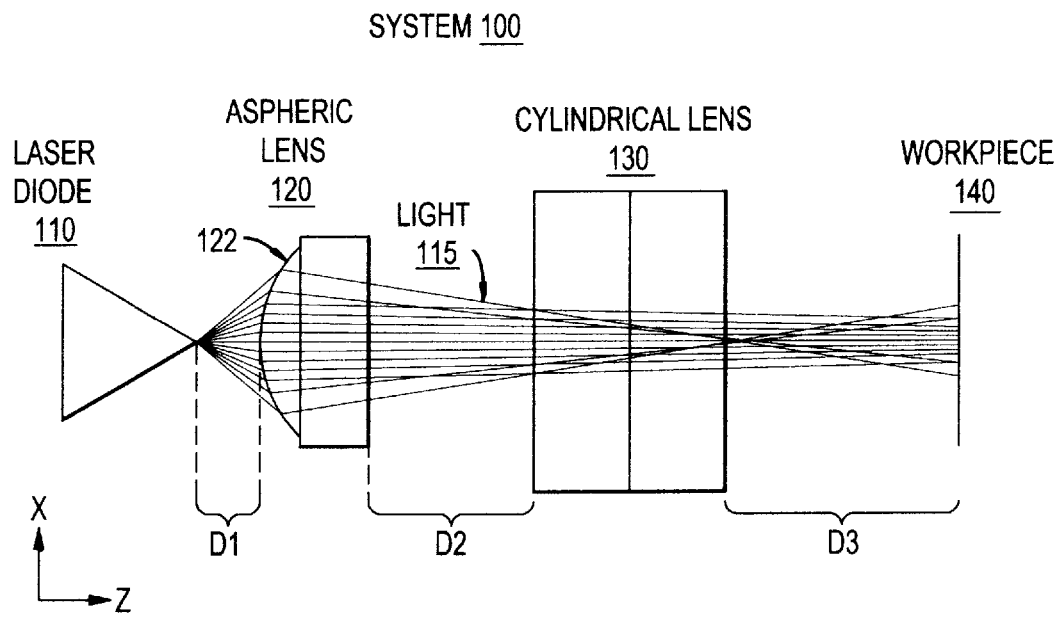
FIGS. 1A-B illustrate an example system for flat-top intensity laser sheet beam generation, in accordance with an embodiment of the present disclosure.

Systems and techniques are disclosed for flat-top intensity laser sheet beam generation. The system includes a source of light directed at a first optical component arranged to receive the light and generate spherical aberration (e.g., third order positive aberration) in the light rays. The spherical aberration results in positive aberrations in the light in a first plane and also results in the light being substantially collimated in a second plane perpendicular to the first plane. In some cases, the source of light is provided from a laser diode and the first optical component is one of an aspherical lens and a spherical lens. The system also includes a second optical component for focusing the light in the second plane. In some cases, the second optical component is a cylindrical lens. In some instances, the third order positive aberration caused by the first optical component shapes the light source to acquire uniform intensity along a laser sheet length direction and the cylindrical lens compresses the laser intensity profile in the sheet thickness direction to achieve the desired profile. Numerous variations and configurations will be apparent in light of this disclosure.

General Overview

Flat-top intensity laser sheet beam, characterized by uniform irradiance distribution along sheet length direction, is important in various laser techniques, such as laser scribing, hole drilling, Particle Image Velocimetry (PIV), Laser-Induced Fluorescence (LIF), hardening, annealing, and cladding, for example. As previously described, the most common laser spatial mode is the TEM00 mode, which delivers a laser beam with a Gaussian profile. To achieve flat-top intensity laser sheet beam, special techniques have to be used to convert the original laser profile, such as the Gaussian profile of a TEM00 mode laser, to the desired flat-top intensity laser sheet profile. Current techniques for achieving flat-top intensity laser profiles require complicated, customized elements, such as absorbing lenses, binary phase grating, deformable mirrors, and specialized diffractive optics, that are difficult to manufacture and are therefore costly. Moreover, the complicated, customized elements also typically require longer working distances to achieve the desired flat-top intensity laser sheet profile.

Thus, and in accordance with one or more embodiments of the present disclosure, systems are disclosed for flat-top intensity laser sheet beam generation. In some embodiments, the flat-top intensity laser sheet profile can be achieved using nonspecialized elements that can decrease the cost of achieving the laser profile and can also allow for smaller form factors compared to other systems. The term "nonspecialized" as used herein in combination with the systems and techniques for flat-top intensity laser sheet beam generation includes spherical, aspherical, and cylindrical optical components, such as lenses. Such nonspecialized elements can be compared to specialized elements used in other techniques for flat-top intensity laser sheet beam generation, such as absorbing lenses, binary phase grating, deformable mirrors, and specialized diffractive optics, to provide a few examples. As previously described, such specialized elements are complicated and highly customized, making such specialized elements difficult and costly to manufacture.

In some embodiments, a flat-top intensity laser sheet profile is achieved by taking a Gaussian profile laser source and using a third order positive aberration to acquire uniform intensity along the laser sheet length direction, in combination with compressing the laser intensity profile in the sheet thickness direction. In some such embodiments, the system includes a laser diode, an aspherical (or spherical) lens, and a cylindrical lens. The laser diode provides the Gaussian profile laser source (e.g., operating in TEM00). The aspherical lens, which is aligned with the laser diode and has its aspherical/ball side facing the laser diode to receive the Gaussian profile laser source, generates third order positive aberration on the laser source. The third order positive aberration caused by the aspherical lens creates a collimated beam with positive aberrations only in a single plane. Typically, spherical aberration (such as third order positive aberration) is avoided in laser systems due to the lack of focus created. However, in the laser systems variously described herein, the spherical aberration helps achieve the flat-top intensity laser profile, as will be apparent in light of the present disclosure. A cylindrical lens receives the beam from the aspherical lens to focus the beam in another plane and to thereby create a flat-top intensity laser sheet profile. The specific laser profile generated may depend on various factors, such as the laser output divergence angles, the laser focal length, the laser size, and the amount of third order aberration caused by the first lens (e.g., by the aspherical or spherical lens). In other words, the aspherical (or spherical) lens generates a flat-top laser profile from the spherical aberration and then the cylindrical lens generates a sheet by focusing the laser in only one direction, where the combination of the two achieves the flat-top intensity laser sheet profile.

In general, the systems and techniques for flat-top intensity laser sheet beam generation variously described herein can be used for various applications, such as laser scribing, hole drilling, Particle Image Velocimetry (PIV), Laser Induced Fluorescence (LIF), hardening, annealing, and cladding, to provide a few example applications. For some such applications, use of a flat-top intensity laser sheet beam profile that has a uniform intensity laser sheet can enable more accurate results and also make the overall process easier to control. In an example application, using a flat-top intensity laser sheet beam profile during laser scribing applications can result in more accurate and uniform trench formation, as well as easier control of the process. In another example application, using a flat-top intensity laser sheet beam profile during scattering applications can result in independence from the laser beam profile, as it is flat (e.g., compared to a Gaussian profile).

In some embodiments, the systems and techniques variously described herein can be used for environmental particulate matter sensor development. The particulate matter sensor measurement technique is based on correlating light scattered by a particulate passing the beam to its particulate's diameter. Therefore, having a uniform intensity beam, such as a flat-top intensity laser sheet beam, can help ensure that the particulate scattering signal is based only on the diameter of the particulate. For example, in the case of a Gaussian (non-uniform) beam profile, the scattered signal from a particulate in an environmental particulate matter sensor measurement application will be based on not only the diameter of the particulate, but also the crossing location of the particulate with the Gaussian laser beam profile, due to the beam not having a uniform intensity, causing the particulate to scatter more light when crossing the centerline of the beam versus toward the edge of the beam. Numerous other applications for uniform intensity beam profiles, such as flat-top intensity laser sheet beam profiles achieved using the systems and techniques variously described herein, will be apparent in light of the present disclosure.

The systems and techniques for flat-top intensity laser sheet beam generation variously described herein provide numerous benefits and advantages. In some embodiments, the systems and techniques use nonspecialized elements that are readily available optical components (e.g., widely available off-the-shelf from various optical components vendors), such as aspherical, spherical, and cylindrical lenses, without the need for specialized elements typically used to generate a flat-top intensity laser sheet profile (e.g., absorbing lenses, deformable mirrors, specialized diffractive elements, etc.). Therefore the systems and techniques can achieve a cost-effective solution for flat-top intensity laser sheet beam generation. Further, the use of readily available nonspecialized optical components can provide the added benefit of easier alignment compared to, for example, techniques for achieving flat-top intensity laser sheet beam generation using specialized elements, as the specialized elements in free space optics require precise and cumbersome alignment to the rest of the system. Moreover, such techniques using specialized elements may require an already collimated laser beam. Further still, the use of readily available optical components can decrease working distances to achieve smaller form factor (e.g., miniaturization) compared to, for example, techniques for achieving flat-top intensity laser sheet beam generation using specialized elements.

The systems and techniques for flat-top intensity laser sheet beam generation variously described herein can be detected in any suitable manner. For example, visual inspection and/or reverse engineering can be used to determine if a laser system includes a laser diode, an aspherical lens, and a cylindrical lens in series. In addition, product literature, advertisements, and other materials related to a laser system can be inspected to determine whether the components of the laser systems variously described herein are present. In some cases, a laser system capable of achieving a flat-top intensity laser sheet profile and having a relatively small form factor laser system compared to conventional systems capable of achieving the laser profile may be a system as variously described herein. Numerous variations and configurations will be apparent in light of the present disclosure.

Example System and Techniques

Figure 1B:
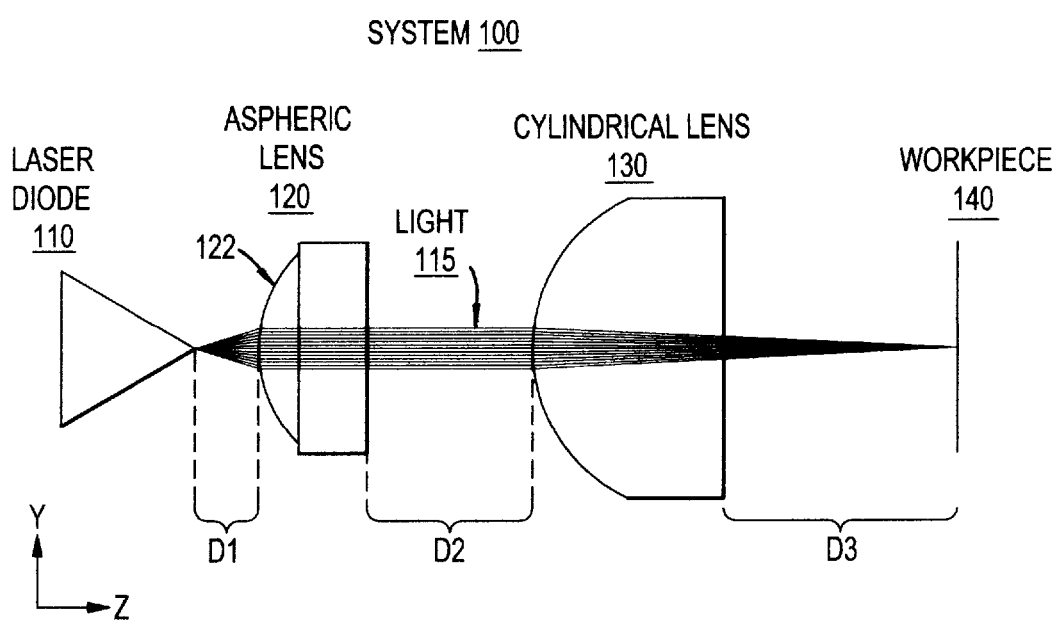

FIGS. 1A-B illustrate an example system 100 for flat-top intensity laser sheet beam generation, in accordance with an embodiment of the present disclosure. Although system 100 is referred to as a system including multiple components, system 100 may be a single device housing all of the componentry of system 100 as variously described herein. As can be seen, in this example embodiment, system 100 includes a laser diode 110, an aspheric lens 120, a cylindrical lens 130, and a workpiece 140. FIG. 1A illustrates the system 100 in an XZ plane with the light 115 ray tracing through the optical elements 120 and 130. FIG. 1B illustrates the system 100 in a YZ plane with the light 115 ray tracing through the optical elements 120 and 130. Note that the YZ plane is perpendicular to the XZ plane. Distance D1 is the distance between the light emitting portion of laser diode 110 and aspheric lens 120, distance D2 is the distance between aspheric lens 120 and cylindrical lens 130, and D3 is the distance between cylindrical lens 130 and workpiece 140. Distances D1, D2, and D3 will also be used to discuss the light 115 in those sections and how the light 115 is affected by optical components 120 and 130. System 100 and the components included therein will be described in more detail below.

In this example embodiment, the light source of system 100 is a laser diode 110. However, in other embodiments, the light source may be some other suitable light source capable of producing laser light. Laser diode 110, in this example embodiment, operates on the fundamental transverse mode or TEM00 mode, thereby emitting a beam that approximates a Gaussian profile. In other embodiments, laser diode 110 may operate in other suitable transverse modes, such as higher-order modes (e.g., TEM01, TEM10, TEM11, TEM02, etc.). The light 115 emitting from laser diode 110 has two different divergence angles: fast and slow axes. In the example system 100 of FIGS. 1A-B, light 115 is propagating in the +Z direction. The laser diode 110 is positioned such that there is a relatively larger divergence angle output in the XZ plane (as shown in FIG. 1A) as a result of the faster divergence axis being in the XZ plane. Further, the laser diode 110 is positioned such that there is a relatively smaller divergence angle in the YZ (as shown in FIG. 1B) as a result of the slower divergence angle output in the YZ plane. Comparing the light 115 emitted from laser diode 110 in section D1 of FIG. 1A versus section D1 of FIG. 1B, it can be seen that the light 115 diverges faster and has a larger angle output in the XZ plane view of FIG. 1A compared to the YZ plane view of FIG. 1B. This alignment will be relevant to the alignment of cylindrical lens 130, as described in more detail below.

System 100, in this example embodiment, includes two optical components: aspherical lens 120 and cylindrical lens 130. As can be seen in FIGS. 1A-B, aspherical lens 120 is positioned with its aspherical (or ball-shaped) side 122 toward laser diode 110, such that light 115 first passes through the aspherical side 122 of aspherical lens 120. As light 115 passes through aspheric lens 120, it generates spherical aberration, and more specifically third order positive aberration. In this manner, aspherical lens 120 is used in an atypical way (e.g., in an opposite fashion than usual), as spherical aberration is generally avoided due to the lack of focus created. In system 100, the spherical aberration is desired to achieve the flat-top profile of light 115, as the spherical aberration causes the rays of light 115 to make large angles relative to the optical axis of system 100. Such rays making significantly large angles with respect to the optic axis are brought to different foci, as can be seen in FIG. 1A (for example, section D3 shows the rays coming to different foci). In some embodiments, a spherical lens can be used in place of aspheric lens 120 in system 100 to create the spherical aberration. However, an aspherical lens oriented as shown in FIG. 1A causes greater spherical aberration compared to a similarly-sized spherical lens, allowing for the working distance to be minimized. The collimated light beam with positive aberrations in the XZ plane (e.g., the light in section D2) then passes through cylindrical lens 130, which only focuses the light 115 in the YZ plane.

Note that although the light 115 is shown in FIG. 1B as perfectly collimated after passing through aspheric lens 120 (e.g., in section D2) such that the light rays are parallel and will spread minimally in the YZ plane as the rays propagate, the present disclosure need not be so limited. In practical applications, it may be difficult or impossible to achieve perfectly collimated light as shown in section D2 of FIG. 1B. For example, in some embodiments, the light in the YZ plane of FIG. 1B may be substantially collimated after passing through aspheric lens 120 such that the rays individually or collectively deviate no more than 0.5, 1, 2, 3, 5, 10, 15, or 20 degrees from exactly parallel, or some other suitable amount, depending on the end use or target application. Further, in some embodiments, substantially collimated may be measured relative to the diameter of aspheric lens 120, such that substantially collimated means that the rays do not spread past the diameter of the lens 120 before a specific distance, such as before at least 1, 2, 3, 5, 10, or 20 times D1 (the distance between the laser diode 110 and the aspheric lens 120), to provide specific examples, or based on some other suitable relative measurement. In some such embodiments, even if the rays spread past the diameter of lens 120, a flat top intensity laser sheet beam can still be generated. However, system 100 may be more efficient in instances where the rays do not spread, or minimally spread, past the diameter of lens 120, as the optical power associated with such rays would be wasted.

In this example embodiment, in the XZ plane illustrated in FIG. 1A, the third order aberration effect is dominant due to the larger laser diode divergence angles in that plane (e.g., as compared to in the YZ plane). As a result, the peripheral rays and paraxial rays do not focus on the same point, causing intensity redistribution and generating the uniform, flat-top profile portion of the flat-top intensity laser sheet beam profile, for example. In the YZ plane illustrated in FIG. 1B, the light beam 115 goes through much less aberration due to orienting the smaller laser diode divergence angles in that plane, and in addition, the light beam in the YZ plane generates a well-focused point where the focal point of the cylindrical lens 130 is located. Accordingly, the cylindrical lens 130 can be used to compress the laser intensity profile in the sheet thickness direction, causing the laser sheet portion of the flat-top intensity laser sheet beam profile, for example. The combination of the flat-top profile in the XZ direction with the uniform, focused point in the YZ direction, a flat-top intensity laser sheet profile can be achieved.

System 100 is highly customizable and configurable, as the components 110, 120, and 130 and the distances D1, D2, and D3 can be selected as desired, depending on the end use or target application. For example, various different laser diodes or laser light sources can be used to provide the light source in system 100, and the properties of the light source may be selected based on the desired power, size, and/or application of system 100. In some cases, the laser diode and laser sheet thickness target may dictate the different combinations of lenses that can be chosen. In some cases, the flat-top intensity generation may depend on the combined effect of laser output divergence angle, focal length, and size and/or the amount of third order positive aberration of the first optical component (e.g., of aspherical lens 120). In some cases, distances D1 and D2, as well as the dimensions of components 110, 120, and 130 in the Z dimension may determine the size of system 100. In some such cases, distance D3 may also contribute to the working distance of system 100, as the distance from cylindrical lens 130 to the workpiece 140 may be considered in the overall space needed for system 100. Numerous variations and configurations will be apparent in light of the present disclosure.

FIGS. 2A-B illustrate example plots 210 and 220 showing experimental results validating the flat-top intensity laser sheet generation of system 100, in accordance with an embodiment of the present disclosure. Plots 210 and 220 were made using a slit based beam scanner to measure the laser beam profile. Plot 210 of FIG. 2A illustrates the laser beam profile in the X-axis and plot 220 of FIG. 2B illustrates a laser beam profile in the Y-axis. The results show a laser sheet having a 2.1 mm×60 microns cross section XY plane size and a flat region in the X direction that covers approximately 2 mm in size (from about 4000 microns to 5800 microns, as can be seen in FIG. 2A). Note that the side peaks shown in plot 210 of FIG. 2A can be removed by clipping (e.g., by passing the beam through an appropriately sized aperture).

Figure 3:
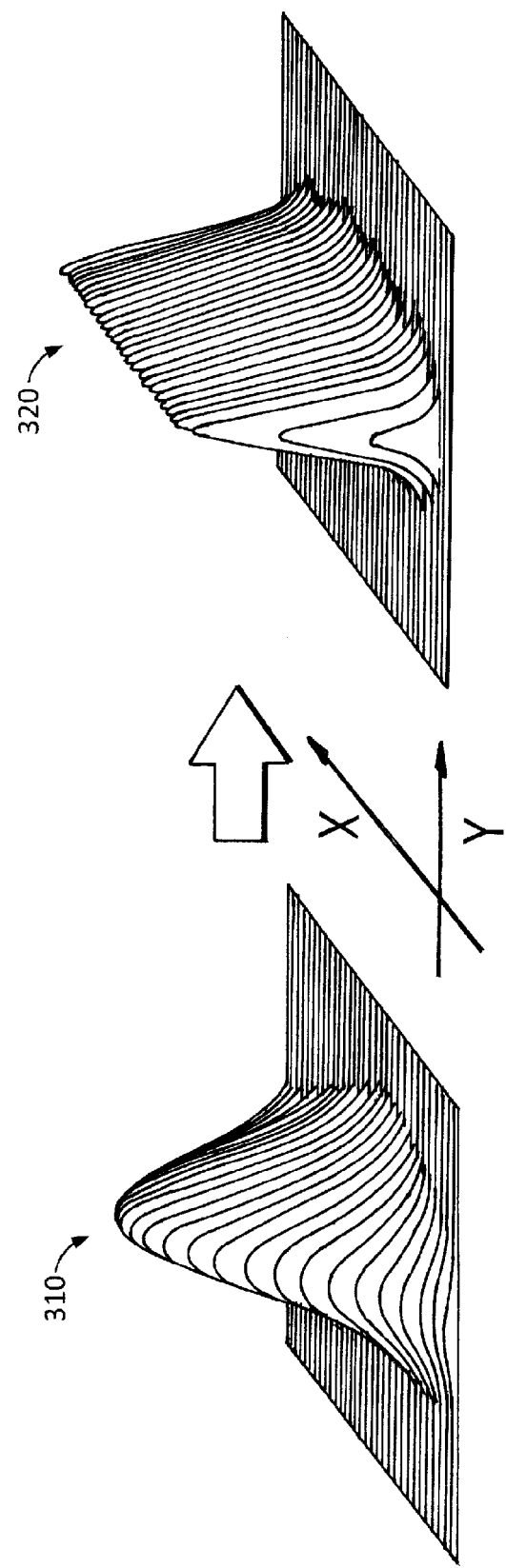
FIG. 3 illustrates laser beam profiles in an XY plane before and after beam shaping using the system of FIGS. 1A-B, in accordance with an embodiment of the present disclosure.

FIG. 3 illustrates laser beam profiles 310 and 330 in an XY plane before and after beam shaping using system 100, in accordance with an embodiment of the present disclosure. Laser beam profile 310 approximates a Gaussian profile, as it is the profile produced by laser diode 110. Laser beam profile 320 is the flat-top intensity laser sheet profile generated by system 100, as a result of laser light from laser diode 110 passing through aspheric lens 120 and then cylindrical lens 130 to cause the beam shaping variously described herein.

Further Example Embodiments

The following examples pertain to further embodiments, from which numerous permutations and configurations will be apparent.

Example 1 is a system for flat-top intensity laser sheet beam generation, the system including: a source of light; a first optical component for receiving the light and generating spherical aberration, resulting in positive aberrations in the light in a first plane and further resulting in the light being substantially collimated in a second plane perpendicular to the first plane; and a second optical component for focusing the light in the second plane.

Example 2 includes the subject matter of Example 1, wherein the spherical aberration is third order positive aberration.

Example 3 includes the subject matter of any of Examples 1-2, wherein the source of light is from a laser diode.

Example 4 includes the subject matter of any of Examples 1-3, wherein the first optical component is an aspherical lens.

Example 5 includes the subject matter of Example 4, wherein the aspherical lens has an aspherical side, and wherein the aspherical side faces the source of light.

Example 6 includes the subject matter of any of Examples 1-3, wherein the first optical component is a spherical lens.

Example 7 includes the subject matter of any of Examples 1-6, wherein the second optical component is a cylindrical lens.

Example 8 includes the subject matter of any of Examples 1-7, wherein the source of light has a larger divergence angle output in the first plane than in the second plane.

Example 9 includes the subject matter of any of Examples 1-8, wherein the source of light approximates a Gaussian profile.

Example 10 includes the subject matter of any of Examples 1-9, wherein the source of light operates in the TEM00 mode.

Example 11 is a an environmental particulate matter sensor including the system of any of Examples 1-10.

Example 12 is a system for flat-top intensity laser sheet beam generation, the system including: a laser diode configured to provide light; an aspherical lens having an aspheric side and arranged to receive the light from the laser diode, wherein the aspheric side is facing the laser diode; and a cylindrical lens arranged to receive the light from the aspherical lens.

Example 13 includes the subject matter of Example 12, wherein the aspherical lens generates spherical aberration resulting in positive aberrations in the light in a first plane.

Example 14 includes the subject matter of Example 13, wherein the aspherical lens further results in the light being substantially collimated in a second plane perpendicular to the first plane.

Example 15 includes the subject matter of any of Examples 12-14, wherein the cylindrical lens focuses the light in a single plane.

Example 16 includes the subject matter of any of Examples 12-15, wherein the cylindrical lens directs the light in a flat-top intensity laser sheet beam profile.

Example 17 includes the subject matter of any of Examples 12-16, wherein the light provided from the laser diode has a larger divergence angle output in a first plane than in a second plane perpendicular to the first plane.

Example 18 includes the subject matter of any of Examples 12-17, wherein the light provided from the laser diode approximates a Gaussian profile.

Example 19 includes the subject matter of any of Examples 12-18, wherein the light provided from the laser diode operates in the TEM00 mode.

Example 20 is an environmental particulate matter sensor including the system of any of Examples 12-19.

Example 21 is a method for flat-top intensity laser sheet beam generation, the method including: providing a source of light; directing the source of light toward a first optical component, the first optical component causing spherical aberration in the light, resulting in positive aberrations in the light in a first plane and further resulting in the light being substantially collimated in a second plane perpendicular to the first plane; and directing the light from the first optical component toward a second optical component, the second optical component causing the light to be focused in the second plane.

Example 22 includes the subject matter of Example 21, wherein the spherical aberration is third order positive aberration.

Example 23 includes the subject matter of any of Examples 21-22, wherein the source of light is provided from a laser diode.

Example 24 includes the subject matter of any of Examples 21-23, wherein the first optical component is an aspherical lens.

Example 25 includes the subject matter of Example 24, wherein the aspherical lens has an aspherical side, and wherein the aspherical side faces the source of light.

Example 26 includes the subject matter of any of Examples 21-23, wherein the first optical component is a spherical lens.

Example 27 includes the subject matter of any of Examples 21-26, wherein the second optical component is a cylindrical lens.

Example 28 includes the subject matter of any of Examples 21-27, wherein the source of light has a larger divergence angle output in the first plane than in the second plane.

Example 29 includes the subject matter of any of Examples 21-28, wherein the source of light approximates a Gaussian profile.

Example 30 includes the subject matter of any of Examples 21-29, wherein the source of light operates in the TEM00 mode.

Example 31 is a particulate matter sensor measurement technique including the method of any of Examples 21-30, wherein the technique is based on correlating light scattered by a particulate passing the laser sheet beam to the diameter of the particulate.

The foregoing description of example embodiments has been presented for the purposes of illustration and description. This description is not intended to be exhaustive or to limit the present disclosure to the precise forms disclosed. Many modifications and variations are possible in light of this disclosure. This disclosure does not intend to limit the scope of the various embodiments. Future filed applications claiming priority to this application may claim the disclosed subject matter in a different manner, and may generally include any set of one or more limitations as variously disclosed or otherwise demonstrated herein.

What is claimed is:

1. A system for flat-top intensity laser sheet beam generation, the system comprising:
    a source of light;
    a first lens for receiving the light and generating spherical aberration, the first lens having an aspherical surface facing the source of light, the first lens resulting in positive aberrations in the light in a first plane and the first lens further resulting in the light being substantially collimated in a second plane perpendicular to the first plane; and
    a second lens for focusing the light in the second plane and not in the first plane, the second lens having a cylindrical surface facing the source of light.

2. The system of claim 1, wherein the spherical aberration is third order positive aberration.

3. The system of claim 1, wherein the source of light is from a laser diode.

4. The system of claim 1, wherein the source of light has a larger divergence angle output in the first plane than in the second plane.

5. The system of claim 1, wherein the source of light approximates a Gaussian profile.

6. The system of claim 1, wherein the source of light operates in the TEM00 mode.

7. An environmental particulate matter sensor comprising the system of claim 1.

8. A system for flat-top intensity laser sheet beam generation, the system comprising:
    a laser diode configured to provide light;
    an aspherical lens having an aspheric side and arranged to receive the light from the laser diode, wherein the aspheric side is facing the laser diode, wherein the aspherical lens generates spherical aberration resulting in positive aberrations in the light in a first plane, and the aspherical lens further results in the light being substantially collimated in a second plane perpendicular to the first plane; and a cylindrical lens arranged to receive the light from the aspherical lens, the cylindrical lens for focusing the light in the second plane and not in the first plane, the cylindrical lens having a cylindrical surface facing the laser diode.

9. The system of claim 8, wherein the cylindrical lens focuses the light in a single plane.

10. The system of claim 8, wherein the cylindrical lens directs the light in a flat-top intensity laser sheet beam profile.

11. The system of claim 8, wherein the light provided from the laser diode has a larger divergence angle output in a first plane than in a second plane perpendicular to the first plane.

12. The system of claim 8, wherein the light provided from the laser diode approximates a Gaussian profile.

13. The system of claim 8, wherein the light provided from the laser diode operates in the TEM00 mode.

14. An environmental particulate matter sensor comprising the system of claim 8.

15. A method for flat-top intensity laser sheet beam generation, the method comprising:

providing a source of light;

directing the source of light toward a first lens, the first lens causing spherical aberration in the light, resulting in positive aberrations in the light in a first plane and further resulting in the light being substantially collimated in a second plane perpendicular to the first plane, the first lens having an aspherical surface facing the source of light; and directing the light from the first lens toward a second lens, the second lens causing the light to be focused in the second plane and not in the first plane, and the second lens having a cylindrical surface facing the source of light.

16. The method of claim 15, wherein the source of light is provided from a laser diode.

17. A particulate matter sensor measurement technique comprising the method of claim 15, wherein the technique is based on correlating light scattered by a particulate passing the laser sheet beam to the diameter of the particulate.

\* \* \* \* \*